(12) United States Patent
Finegold

(10) Patent No.: US 9,168,275 B2
(45) Date of Patent: Oct. 27, 2015

(54) **METHOD OF TREATING GASTROINTESTINAL DISEASES ASSOCIATED WITH SPECIES OF GENUS *CLOSTRIDIUM***

(75) Inventor: Sydney M. Finegold, Marina Del Rey, CA (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 1622 days.

(21) Appl. No.: 11/979,007

(22) Filed: Oct. 30, 2007

(65) Prior Publication Data

US 2008/0254009 A1 Oct. 16, 2008

Related U.S. Application Data

(63) Continuation of application No. 10/297,131, filed as application No. PCT/US01/18071 on Jun. 5, 2001, now abandoned.

(60) Provisional application No. 60/209,712, filed on Jun. 5, 2000, provisional application No. 60/214,813, filed on Jun. 28, 2000, provisional application No. 60/240,582, filed on Oct. 16, 2000.

(51) Int. Cl.

| | | |
|---|---|---|
| *A61K 39/00* | (2006.01) |
| *A61K 39/38* | (2006.01) |
| *A61K 39/02* | (2006.01) |
| *A61K 39/08* | (2006.01) |
| *A61K 35/745* | (2015.01) |
| *A61K 31/43* | (2006.01) |
| *A61K 31/545* | (2006.01) |
| *A61K 31/7048* | (2006.01) |
| *A61K 35/741* | (2015.01) |
| *A61K 35/742* | (2015.01) |
| *A61K 35/744* | (2015.01) |
| *A61K 35/76* | (2015.01) |
| *A61K 38/00* | (2006.01) |

(52) U.S. Cl.
CPC ............... *A61K 35/745* (2013.01); *A61K 31/43* (2013.01); *A61K 31/545* (2013.01); *A61K 31/7048* (2013.01); *A61K 35/741* (2013.01); *A61K 35/742* (2013.01); *A61K 35/744* (2013.01); *A61K 35/76* (2013.01); *A61K 38/00* (2013.01); *A61K 39/00* (2013.01); *C12N 2795/00032* (2013.01)

(58) Field of Classification Search
CPC ... A61K 2300/00; A61K 48/00; A61K 45/06; C07K 2319/00; C07K 2317/34; C07K 2316/96; C07K 2317/21
See application file for complete search history.

(56) References Cited

U.S. PATENT DOCUMENTS

| | | |
|---|---|---|
| 4,710,379 A | 12/1987 | Kawai et al. |
| 5,443,826 A * | 8/1995 | Borody ........................ 424/93.3 |
| 5,925,550 A | 7/1999 | Lancini et al. |
| 5,948,402 A | 9/1999 | Keith et al. |
| 6,696,057 B1 | 2/2004 | Bojrab |
| 2001/0036453 A1 | 11/2001 | Reid et al. |
| 2004/0028689 A1 | 2/2004 | Borody |
| 2004/0167062 A1 | 8/2004 | Bolte |
| 2004/0170617 A1 | 9/2004 | Finegold |

OTHER PUBLICATIONS http://www.neurologychannel.com/autism/treatment.shtml.*
http://www.mayoclinic.com/health/autism/DS00348/DSECTION=treatments%2Dand%2Ddrugs.*
Bolte (Medical Hypotheses, 1998; 51(2): 133-144).*
Sandler et al. (J. Child. Neurol., 2000; 15: 429-435). abstract only.*
Sandler et al., Pediatric Research, 1998; 43: 105-105 (abstract).*
Sullivan, A. et al. "Probiotics and gastrointestinal diseases". Journal of Internal Medicine 2005; 257: pp. 78-92. Blackwell Publishing Ltd.

* cited by examiner

*Primary Examiner* — Gary Nickol
*Assistant Examiner* — Lakia Tongue
(74) *Attorney, Agent, or Firm* — Adriano & Associates

(57) ABSTRACT

The invention includes a method of treating gastrointestinal diseases associated with species of genus *Clostridium* such as *clostridium* deficit in human patients with gastrointestinal disorders having an etiological component such as a microbial agent producing a toxin where treated with an antimicrobial composition an amount effective to inhibit or eliminate the microbial agent. The antimicrobial composition in a form of probiotic mixture can be administrated alone or in combination with an antimicrobial agent, such as a bacteriophage which is specific for a bacterium producing toxin or antibiotics which are then used to eliminate or inhibit the clostridial species overgrown in a patient's gastrointestinal tract. Disorders that can be treated by the method of the invention include diarrhea or inflammatory bowel diseases such as colitis or Crohn's disease.

5 Claims, 1 Drawing Sheet

| NO. OF SPECIMENS HARBORING | |
|---|---|
| 23 | ESCHERICHIA COLI |
| 23 | ENTEROCOCCI |
| 15 | OTHER STREPTOCOCCI |
| 23 | BACILLUS SPECIES |
| 25 | BACTEROIDES FRAGILIS |
| 24 | EUBACTERIUM |
| 19 | BIFIDOBACTERIUM |
| 24 | CLOSTRIDIUM |
| 24 | ANAEROBIC COCCI |
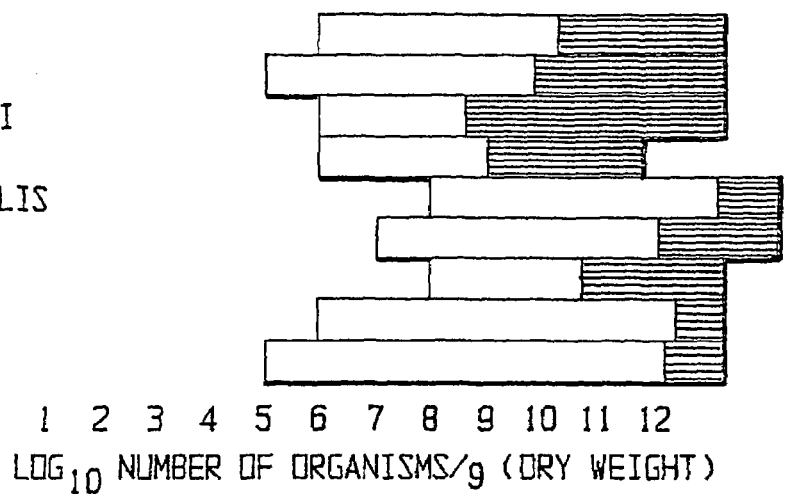
$LOG_{10}$ NUMBER OF ORGANISMS/g (DRY WEIGHT)

METHOD OF TREATING GASTROINTESTINAL DISEASES ASSOCIATED WITH SPECIES OF GENUS CLOSTRIDIUM

CROSS-REFERENCE TO RELATED APPLICATION(S)

This application is a continuation of U.S. patent application Ser. No. 10/297,131, filed Oct. 7, 2003, which is an U.S. national phase of International Application No. PCT/US01/018071, filed Jun. 5, 2001, which claims priority of U.S. Provisional Application Ser. No. 60/209,712 entitled "Method for Treating Autism" filed Jun. 5, 2000 and U.S. Provisional Application Ser. No. 60/214,813 entitled "Therapies for Gastrointestinal and Neurological Disorders" filed Jun. 28, 2000, and Addition 1 Ser. No. 60/240,582 filed Oct. 16, 2001 to said prior filed provisional applications. The subject matter of each of said applications is incorporated herein by reference in its entirety.

BACKGROUND OF THE INVENTION

The composition of the normal gastrointestinal flora varies somewhat from individual to individual. Some bacterial species may be carried only transiently, but most are fairly permanent. Some members of the normal flora can become pathogenic if they acquire additional virulence factors (e.g., *E. coli*) or are introduced into normally sterile sites (e.g., *Staphylococcus aureus*). Normal flora is general beneficial—for example, the normal flora may prevent pathogenic microorganisms from proliferating in the body (a phenomenon known as colonization resistance), and may also produce essential nutrients (e.g., vitamin K is produced by the gut flora).

The use of antibiotics is ubiquitous among children and adults for bacterial infections, and they are often also prescribed for viral infections. This prolific use has come under criticism for various reasons, most notably for inducing microbial resistance to previously effective antibiotics and rendering them less effective or ineffective against dangerous human pathogens. For example, multidrug-resistant strains of *Mycobacterium tuberculosis* seriously threaten tuberculosis (TB) control and prevention efforts. Administration of broad-spectrum antibiotics has a profound effect on the normal flora and can result in colonization with antibiotic-resistant organisms. Antibiotic-mediated disruption of the normal flora can lead to fungal infections, such as invasive candidiasis, or to antibiotic-associated colitis caused by *Clostridium difficile*.

Members of the genus *Clostridium* are Gram-positive, spore-forming anaerobic rods. These bacteria are ubiquitous in nature (including the human colon) and are readily found in soil. When stressed, the bacteria produce spores that tolerate extreme conditions that the active bacteria cannot. In their active form, some of these bacteria secrete powerful exotoxins that are responsible for such diseases as tetanus, botulism, and gas gangrene. Clinically important species of *Clostridium* include *C. tetani*, *C. difficile*, *C. perfringens* and *C. botulinum*, as well as several others.

SUMMARY OF THE INVENTION

The invention includes a method of preventing or treating a gastrointestinal or neurological disorder other than delayed-onset autism in a patient, the disorder having as an etiological component a microbial agent, the method comprising administering to the patient an antimicrobial composition in an amount effective to inhibit or eliminate the microbial agent. By "microbial agent" is meant a microbe or its toxin. Disorders that can be treated by the methods of the invention include Attention Deficit Disorder, Depression, bipolar disorder, Alzheimer's disease, Parkinson's Disease, Whipple's Disease, Tourette's Syndrome, Asperger's syndrome, Pervasive Development Disorder, early onset autism, Rhett's Syndrome, D-lactic acidosis, and schizophrenia. Gastrointestinal disorders can include antimicrobial associated diarrhea or inflammatory bowel diseases such as ulcerative colitis or Crohn's disease. The method can be used where the agent is a species of the genus *Clostridium* or produces a toxin having some homology with a toxin from *Clostridium*.

The antimicrobial composition preferably has at least one of the following properties: oral palatability, sustained concentration throughout the gastrointestinal tract, low absorption from the gut (and hence low systemic concentration), higher activity against *Clostridium* relative to activity against other normal gut flora, bactericidal activity, not cross-resistant with vancomycin or other antimicrobials that are important for treatment of systemic infections, resistance does not develop readily, the composition is well tolerated orally and over an extended period of time (preferably at least 3-4 months), it is effective when given once or twice daily, has low systemic and gastrointestinal toxicity, and is economical. A preferred composition is Ramoplanin.

An alternative or supplemental therapy involves the use of a bacteriophage in addition to or as the antimicrobial composition. The bacteriophage is preferably specific for the pathogen that is overgrown and producing the toxin. This is preferably a member of the genus *Clostridium*.

Another alternative or supplemental method of treating a neurological or gastrointestinal disorder is a therapy regimen to repopulate the gastrointestinal tract with normal flora. This therapy comprises feeding the patient with at least one of the normal gut inhabitants that is present in healthy people in high numbers.

In another embodiment, the invention includes a method of detecting a neurological or gastrointestinal disorder that has as an etiological component a microbe that produces a toxin having at least some homology with tetanus toxin. The method comprises collecting a sample from a patient suspected of having such disorder, and screening the sample with an antibody directed against a conserved epitope of the tetanus toxin, where a specific interaction of the antibody with the sample indicates the presence of a neurological disorder in the patient. An alternative embodiment is the use of an antibody generated against the specific toxin causing the neurological or gastrointestinal disorder. Such an antibody can be produced by conventional means (e.g., polyclonal, monoclonal), or can be derived from a patient having a high serum titer to the causitive agent.

Another feature of the invention is a method of treating or preventing a neurological or gastrointestinal disorder in a patient, the disorder having as an etiological component a microbe that produces a toxin, the method comprising vaccinating the patient with an antigenic epitope of the toxin such that an immune response capable of interaction with gut flora (e.g., via Peyer's patches, IgA, or other complement activation local to the gut) can be elicited upon antigen challenge from microbe proliferation in the gut.

Another feature of the invention is a DNA encoding a polypeptide comprising a novel toxin produced by a member of the genus *Clostridium*.

DETAILED DESCRIPTION OF THE INVENTION

It has been discovered that disruption of gastrointestinal flora or poorly developed gastrointestinal flora in young infants and subsequent pathogenic microbial proliferation in one or more regions of the gastrointestinal tract can mediate a variety of disruptions of neurological function. These neurological disruptions are mediated by toxins, particularly neurotoxins, produced by one or more species of the proliferating microbes. Bacteria of the genus *Clostridium* are indicated as the likely causative agents, and toxins having at least some homology to the known neurotoxins of e.g., *Clostridium tetani* and *Clostridium botulinum* mediate the neurologic effects. These clostridial toxins are potent, non-necrotizing neurotoxins that disrupt neurotransmitter release. However, it is possible that another or genera could be causative organism(s), although a neurotoxin is the likely agent causing the neurological symptoms. Neurotoxins such as the neuromuscular transmission inhibitor tetanospasmin, produced by *C. tetani*, have traditionally been considered to be dangerous following systemic exposure only (e.g., exposure by introduction of the bacterium or spores into a wound, for example).

It has also been discovered that the methods of the invention, including antibiotic therapy directed to the proliferating microbial species, results in improved neurological function through inhibition or elimination of the proliferating species. Recurrence of the neurological symptoms can be limited or prevented by repopulation of the gastrointestinal tract by normal human gut flora ("probiotic therapy"). The neurological syndromes themselves can be prevented or limited in the place by appropriate probiotic therapy following administration of wide spectrum antibiotics, especially in children or compromised adults. Alternatively, limiting the use of broad-spectrum antibiotics can also help prevent the widespread disruption of the gastrointestinal flora at the outset. Finally, vaccination leading to a gut level immunoresponse against toxin antigens responsible for the neurologic symptoms can be used to prevent occurrence of disorders due to microbial overgrowth.

The pathogenic proliferation of microbes in the gut can at least partially cause deleterious neurological symptoms and syndromes of many disorders, including at least some forms of Pervasive Development Disorder including both Early-Onset and Late-Onset Autism; Asperger's syndrome; Attention Deficit Disorder; Depression; Bipolar Disorder; Alzheimer's Disease; Parkinson's Disease; Whipple's Disease; Tourette's Syndrome; Rhett's Syndrome; and Schizophrenia.

Additional diseases and disorders are also caused by disrupted gut microbial flora, and can be treated and/or prevented by antibiotic and probiotic measures. Examples of such disorders include antibicrobial associated diarrhea and inflammatory bowel disease (including, for example, ulcerative colitis and Crohn's Disease). A very important example is hospital-acquired (nosocomial) systemic infection due to *S. aureus, Pseudomonas, Klebesiella-Enterobacteria*, etc. which may often be traced to previous colonization of the intestinal tract by these organisms following hospitalization.

Many, if not most, of the disorders mentioned above are clearly unrelated by conventional medical knowledge and/or standards. However, the surprising discovery of a common etiology makes possible a common diagnostic, therapeutic, and preventative concept, embodied in the methods of the invention.

Clostridia as Causative Agents

Members of the genus *Clostridium* are plausible as agents of these neurological disorders, because several members of this genus are known to produce neurotoxins, they proliferate enterically during antimicrobial therapy (e.g., *C. difficile*), and they have been implicated in diarrheal diseases of humans and animals. For example, *Clostridium tetani* is the bacterium that causes tetanus (lockjaw) in humans. *C. tetani* spores can be acquired from any type of skin trauma involving an infected device. If an anaerobic environment is present, the spores will germinate and eventually form active *C. tetani* cells. At the tissue level, the bacterium then releases an exotoxin called tetanospasmin that causes certain nervous system irregularities by means of retrograde transmission through neurons to the nervous system. One of the toxin's classic effects includes constant skeletal muscle contraction due to a blockage of inhibitory interneurons that regulate muscle contraction. Prolonged systemic infection eventually leads to respiratory failure, among other things. If not treated early, the mortality rate of this disease is high.

*Clostridium botulinum* produces one of the most potent toxins in existence and causes botulism food poisoning. Infantile botulism is much milder than the adult version and generally occurs before the age of 9-12 months, when children develop a full complement of normal gut flora. Honey is the most common source of the spores, which germinate in the child's intestinal tract. Bacterial proliferation and subsequent toxin production cause symptoms which last a number of days and eventually subside, sometimes without the use of an antitoxin.

*C. perfringens* is a non-motile bacterium and an invasive pathogen that is present in the normal bowel flora and can also be acquired from dirt via large cuts or wounds. *C. perfringens* cells proliferate after spore germination occurs and they release their exotoxin. The toxin causes necrosis of the surrounding tissue. The bacteria themselves produce gas which leads to a bubbly deformation of the infected tissues. *C. perfringens* is capable of necrotizing intestinal tissues and can release an enterotoxin that may lead to severe diarrhea.

*Clostridium difficile* is a motile bacterium that can be part of the natural intestinal flora, but may also be acquired from the environment or by cross-infection in the hospital setting. Infection can occur through the use of broad-spectrum antibiotics which lower the relative amount of other normal gut flora. When this situation occurs, *C. difficile* proliferates and infects the large intestine. The bacterium then releases an enterotoxin and a cytotoxin that destroy the intestinal lining and cause diarrhea. The preferred method of treatment is metronidazole vancomycin or both given orally.

Although members of this genus, as exemplified above, generally are pathogenic systemically, a subtler syndrome can occur upon subacute, chronic, enteric infection with the above or related organisms. Clostridia or other microbes capable of producing a neurotoxin and proliferating opportunistically are likely candidates to cause the neurological disorders discussed above, and are susceptible to treatment or preventative measures using the methods of the invention. They may also produce an enterotoxin that leads to gastrointestinal symptomatology.

Recognition of the gastrointestinal component of these neurological disorders allows diagnosis and treatment of a novel and specific nature.

Diagnosis

Diagnostic options include tests based on detection of the gene that codes for the toxin produced by the overgrown microbe, the toxin itself, or proliferation of a particular toxin-producing microbe. Such tests include amplification of nucleic acids encoding the toxin (e.g., by PCR, using printers specific for the toxin or toxins of interest; specific hybridization assays (e.g., in situ hybridization; Northern, Southern, or dot blots; microarray hybridization, etc.); detection of the toxin itself using, e.g., anti-toxin antibodies, (generated monoclonally, polyclonally, or derived from patients with high titers of anti-toxin antibodies (such antibodies are likely to be better reagents than commercial tetanus antibodies or antibodies generated against conserved regions of multiple bacteria, since they will be exceptionally specific for the causative toxin) in ELISAs, sandwich assays, Western blots, or affinity chromatography; animal assays; laser mass spectroscopy, or any other methods known to those of skill in the art. Samples can be obtained from fecal samples, blood, plasma, urine, saliva, cerebrospinal fluid, biopsy tissue, or any other patient source, and may be directly tested or after isolation of suspected causative agents.

Screening assays are based on detection of suspect organisms in the feces of patients using culture and microbiologic identification techniques, immunofluorescent techniques, genetic probes, laser mass spectroscopy, or other methods known in the art.

Selection of Antimicrobial Therapeutic Agents

Antimicrobials to Treat Disorders Resulting from Disrupted Gut Flora

Once a positive diagnosis has been made, antimicrobial therapy can be started to inhibit or eliminate the microbe whose enteric overgrowth and/or toxin production is causing the disorder. The antimicrobials used to treat the disorders described above should have certain characteristics for optimal benefit and minimal side effects. Certain antimicrobials have characteristics appropriate to treat even very young children, and such drugs are useful to treat disorders having the gut-brain involvement. Preferably, an antimicrobial selected as a therapy for any of the above disorders will have one or more of the following properties:

1. Good in vitro activity against most or all clostridial species;
2. Relatively poor activity against most other organisms normally found in the gut flora;
3. Safe doses capable of achieving a concentration in the colon exceeding the minimal inhibitory concentration or minimal bactericidal concentration of the 20 drug by at least four or five two-fold concentrations;
4. Preferably absorbed very little or not at all when given orally (to minimize systemic effects;
5. Bactericidal activity preferred (rather than purely inhibitory activity);
6. Not cross-resistant with vancomycin or other drugs that are important for treatment of systemic infections;
7. Resistance doesn't develop readily: (i.e., the drug doesn't readily engender resistance in bacteria);
8. Palatable in liquid form when taken orally (for administration to children), or readily formulated into other oral doses (to enhance patient compliance);
9. Well tolerated orally over extended period of time (preferably at least 3-4 months);
10. Little or no toxicity, either systemically or in the bowel;
11. Preferably effective when given only once or twice daily; and
12. Preferably moderate in price Drugs that have one or more of the above characteristics may have utility for antimicrobial therapy in treating neurological disorders with a gut flora etiology include those listed below:

ABT-773
Ampicillin/sulbactam
Amphomycin
Azithromycin
Bacitracin
Carbomycin
Cephalosporins, oral -continued Clarithromycin
Erythromycins
Furazolidone, other nitrofurans
Fusidic acid, Na fusidate
Gramicidin
Imipenem, oral; other penems
Josamycin
Linezolid, other oxazolidinones
Macrolides
Metronidazole, other nitroimidazoles
Mikamycin
Novobiocin
Oleandomycin, triacetyloleandomycin
Ostreogrycin
Pristinamycin
Ramoplanin
Ristocetin
Rosamicin, rosaramicin
Spectinomycin
Spiramycin
Staphylomycin
Streptogramin
Synergistin
Teicoplanin
Telithromycin
Ticarcillin/clavulanic acid
Tyrocidin
Tyrothricin
Vancomycin
Vernamycin
Virginiamycin Piperacillin/Tazobactam Appropriate doses of these antimicrobials are within the range given for many other conditions for which the antimicrobials are prescribed. Dosage information can be found, for example, in the Physicians' Desk Reference, 54th Edition, Medical Economics Company, Montvale, N.J. (2000). In certain instances, the doses may be elevated to the extent necessary to maintain a bactericidal or bacteriostatic concentration throughout the gastrointestinal tract. The antimicrobials are preferably formulated for oral administration, such as in liquid form, tablet, capsule, granules, chewable, etc. Tablets or capsules may be enterically coated to minimize gastricabsorption of the drug (since very few bacteria are capable of colonizing the stomach, this is not necessarily a primary target of the therapies of the invention).

A preferred compound for treating *Clostridium* sp. overgrowth in the gut is ramoplanin, also known as A-16686 (see, e.g., U.S. Pat. Nos. 4,303,646; 4,328,316; 4,427,656; 5,539,087; and 5,925,550; and Parenti et al.; *Drugs Exp Clin Res* 16(9):451-5 (1990); all herein incorporated by reference). This antibiotic is not cross-resistant with vancomycin, it engenders very little to no resistance in bacteria, is not detectably absorbed systemically in humans (making it exceptionally safe, even for young children), can be made palatable in a liquid form, achieves high concentrations in the large intestine, has very good activity against clostridia, can be given twice a day, and is only active against gram positive organisms at the dosage levels administered. Ramoplanin is preferable to drugs such as vancomycin and metronidazole, which have previously been used, because, for example, vancomycin, while achieving a high concentration in the intestines throughout, is effective against *Bacteroides*, a beneficial genus of gut flora, as well as clostridial species. It is also a potent antibiotic against, e.g., systemic methicillin-resistant *Staphylococcus* infections, and widespread use for other purposes risks inducing vancomycin-resistant *Staphylococcus* species. Metronidazole, on the other hand, is not an ideal candidate because of its ready systemic absorption, which can lead to neurotoxic side effects when given in high enough concentrations to remain effective in the gut, and the fact that it is quite bitter and thus difficult to formulate as a liquid for oral use.

Therapies to Prevent Occurrence of Pathogenic Bacterial Overgrowth and Attendant Disorders It is desirable to prevent, rather than merely treat, the gastrointestinally mediated neurological disorders discussed herein, by reducing the extent of normal bacterial disruption in the gut during antimicrobial treatment for other infections. This can be done by not using antibiotics for viral or other non-bacterial infections, but if an antibiotic must be used, it should be tailored as specifically as possible against the identified or most likely causative agent.

For example, one common drug to avoid in treating infections in young children is trimethoprim/sulfamethoxazole because it has been anecdotally indicated by parents of late onset autistic children as the most common background factor (use of this antimicrobial for, e.g., ear infections, just prior to onset of autistic symptoms). This drug has also been shown to cause major overgrowth of clostridia in the bowel flora of adults (see, e.g., Haralambie et al., Infection 11(4):201-4 (1983). On the other hand, a drug such as ampicillin would have a good spectrum of activity against the pathogens of otitis media (principally *Streptococcus pneumoniae* and *Haemophilus influenzae*) and is also active against clostridia, so would not likely to lead to overgrowth of clostridia in the bowel flora.

It is important to use agents with as narrow and specific a spectrum as possible for the disorder being treated. A different or supplemental approach (discussed more fully below) is to replenish the eliminated flora as quickly as possible with probiotic treatment to prevent overgrowth of the problem clostridia.

Another approach is to immunize children in such a way that they obtain immunity at the level of the gut mucosa to the toxin involved. This involves eliciting at least immunoglobulin A (IgA) response specific against exposed antigens of the *Clostridium* toxin or toxins. Cell-mediated immunity is also important in mucosal immunity to various pathogens (van Ginkel et al., *Emerging Infect. Dis.*, 6:123-132, 2000. The pathogenic effect of overgrowth of the bacterial species involved (those producing the neurotoxins), even if it occurs, is then rendered harmless by the immune response against the toxin locally, at the gut where the toxin is produced. Eliciting this response (e.g., via B cells aggregated in the Peyer's patches/lymph nodules of the intestine) involves an antitoxin to the toxin, toxoid, or modified toxin that would induce immunity to the toxin. The data provided in the Examples below demonstrate that one or more toxins with homology to tetanus toxin (tetanospasmin) are responsible for the neurological symptoms seen in, e.g., late onset autistic children, and a region of high homology among two or more toxin genes is the preferable region or epitope to use to induce the antigenic response.

Since tetanus toxin is a member of the family of zinc endopeptidases, the use of a selective synthetic or natural zinc endopeptidase inhibitor is also a therapeutic option to reverse or prevent the neurological effects of chronic subacute *Clostridium* infection and resultant toxin release. Examples of pseudotripeptide compounds useful in this respect, containing an ethylene sulfonamide or an m-sulfonamidophenyl moiety as the P1 side chain and natural amino acids in the P1' and P2' components, can be found in Martin et al., *J. Med. Chem.,* 42(3):515-525 (1999), herein incorporated by reference. Captopril, an oral medication well tolerated by children, is such an inhibitor and inactivates tetanus toxin in vitro.

As a last resort, surgical or pharmacologic vagotomy may be used in especially refractory cases of neurologic disorder caused by clostridial neurotoxin. The rationale is that tetanus toxin is known to travel retrogradely up the vagus nerve (which innervates the gastrointestinal tract), and vagotomy would prevent transmission of toxin from the gut to the brain, thus alleviating the neurological symptoms and preventing recurrence.

Probiotic Therapy

A preferred therapy, however, alone or in conjunction with one or more of the therapies discussed herein, is probiotic therapy. "Probiotic" therapy is intended to mean the administration of organisms and substances which help to improve the environment of the intestinal tract by inhibiting the disproportional growth of bacteria which produce toxins in the intestinal tract. For example, in healthy humans, the small intestine is colonized by lactobacilli (e.g., *L. acidophilus*), *Bifidobacterium*, gram-negative anaerobes, enterococci, and Enterobacteriaceae; the large intestine is colonized mainly by obligate anaerobes (e.g., *Bacteroides* sp., gram-positive anaerobic cocci, *Clostridium* sp., Enterobacteriaceae (mainly *E. coli*), and enterococci. These bacteria produce substances which suppress harmful bacteria; for example, bifidobacteria produce lactic and acetic acid, decreasing the pH of the intestines. They can also activate macrophages, which also help suppress harmful bacteria.

The best strains for supplementation are those that are typically permanent residents of the human intestinal tract and which do not produce toxins. Normal human intestinal flora are better adapted to the environment (bile acids, anaerobic conditions, etc.) of the human intestinal tract, and are more likely to survive and colonize the human intestinal tract. Certain species such as *L. bulgaricus* and *S. thermophilus*, for example, are commonly used as probiotics, but are not normal constituents of human gut flora, and such species apparently do not colonize the intestinal tract well.

The probiotic therapy of the invention is designed to be administered as a mixture of a large number of species that are normal, benign inhabitants of the gut, preferably in the general proportion in which they are found in healthy humans. For example, *E. coli* is a common enteric inhabitant, but makes up only about 1/1000 of the bowel flora found in healthy humans, so would be a relatively small proportion of a probiotic mixture. Description of normal human gut flora and relative abundances can be found in FIG. 2, the tables below and Finegold, *J. Assoc. Anaerobic. Infect. Res.* 28:206-213 (1998); and Finegold, et al., Normal Indigenous Intestinal Flora, Chap. 1, in Hentges, D. J., ed. *Human Intestinal Microflora in Health and Disease*, New York, Academic Press, p. 3-31, 1983; both herein incorporated by reference.

TABLE 1

Prevalence of major organisms in fecal flora

| | % Stools Positive | Mean Count/gm ($Log_{10}$) |
|---|---|---|
| Gram-negative anaerobic rods | 100 | 11.3 |
| Gram-positive NSF* anaerobic rods | 99 | 11.1 |
| Anaerobic cocci | 94 | 10.7 |
| *Clostridium* | 100 | 9.8 |
| *Streptococcus* | 99 | 8.9 |
| Gram-negative aerobic or facultative rods | 98 | 8.7 |
| Other aerobic or facultative organisms | 93 | 6.8 |

*NSF = Nonsporeforming

TABLE 2

Most prevalent species in fecal flora

| | % Stools Positive | Mean Count/gm (Log$_{10}$) |
|---|---|---|
| *Bacteroides thetaiotaomicron* | 87 | 10.7 |
| *Bacteroides vulgatus* | 70 | 10.6 |
| *Bacteroides distasonis* | 53 | 10.5 |
| *Bacteroides fragilis* | 46 | 10.4 |
| *Bifidobacterium adolescentis* group | 55 | 10.0 |
| *Eubacterium aerofaciens* | 49 | 9.7 |
| *Clostridium ramosum* | 53 | 9.1 |
| *Escherichia coli* | 93 | 8.6 |
| *Streptococcus faecalis* group | 80 | 7.5 |

A suitable probiotic mixture is composed of at least one, preferably at least three, more preferably a larger number, of the species listed in Table 2 and others in about the proportions found normally in the colon (see list in the "Mean Count/gm" column). It is estimated that, in all, there may be 300-400 species found in human colonic flora.

Dosage (colony forming units (cfu) of each bacterium) is preferably at least the number found in the mean count/gram, and is supplied to the patient daily or twice daily for a number of days until it is determined that the bacteria have become established. The formulation can be provided as active cells or spores. It can be provided in an enterically coated form (e.g., for active cells) to protect sensitive cells from the gastric environment. A preferred therapy involves temporary elimination or suppression of the patient's flora (primarily or entirely with the use of antimicrobial agents) and introduction of a new, non-pathogenic flora that consists of a number of bacteria normally found in the bowel that convey colonization resistance (to prevent regrowth or re-implantation of the offending bacteria). Therapies are preferably patterned after those described in the poultry literature, for example, Wooley et al., *Avian Dis.* 43(2):245-50, (1999); Hume et al., *J. Food Prot.* 61(6):673-6 (1998); Corrier et al., *J. Food Prot.* 61(7): 796-801 (1998); Hume et al., *Avian Dis.* 40(2):391-7 (1996); Corrier et al., *Poult Sci.* 74(7):1093-101 (1995); and Corrier et al., *Poult Sci.* 74(6):916-24 (1995), all herein incorporated by reference.

Alternatively, bacteriophage specific for the bacterium producing the toxin can be introduced to the patient's gastrointestinal tract to reduce or kill the toxin-producing bacteria, and probiotic therapy mixtures can be concurrently or subsequently administered. An example of a successful protocol involving this strategy with *Clostridium difficile* can be found in Ramesh et al., *Anaerobe* 5:69-78 (1999), herein incorporated by reference. Bacteriophage may be susceptible to gastric acidity and such acidity should be neutralized prior to phage administration, or else the bacteriophage can be administered in an enterically coated tablet or capsule.

Probiotic therapy can be used in conjunction with antimicrobials used to treat infections in otherwise normal patients (i.e., before the onset of aneurological disorder) in order to prevent or reduce the risk of the occurrence of a neurological disorder. Alternatively, it can be used in conjunction with antimicrobials being used to eliminate or inhibit the clostridial species overgrown in a patient's gastrointestinal tract, and to promote the re-emergence of normal gut flora and proportions/balance.

The following Examples are intended to be illustrative rather than encompassing.

Example 1

Results in Autistic Children

Experiments conducted with late-onset autistic children (Sandler et al., *J. Child Neurol.* [cite] (2000), herein incorporated by reference) have demonstrated success using methods of the invention. The inventors have recorded significant improvement in the symptoms of children with delayed-onset autism by providing them with antibiotics directed toward common anaerobic intestinal bacteria. By "delayed-onset," "regressive," or "late onset" autism is meant specifically an autism syndrome that appears in a child (generally between 12 and 18 months old) who has previously been developing normally. Symptoms include loss of language, social, and play skills, and onset of autistic characteristics such as avoidance of eye contact, self-stimulation behaviors, etc. Other forms of autism are clinically distinct in onset, for example early onset autism, where affected children may be born with the autistic condition or it may develop very early in life. Conventional theories are that there are genetic underpinnings to early onset autism, but it is more likely in at least some cases that there is a gastrointestinal component, for example, infection with toxin-producing organisms because of a net yet fully developed normal flora (as in infant-botalism).

Eleven children with regressive onset autism were recruited for an intervention trial using a minimally absorbed oral antibiotic. Entry criteria included antecedent broad-spectrum antimicrobial exposure, followed by chronic persistent diarrhea, deterioration of previously acquired skills, and then autistic features. Short-term improvement was noted using multiple pre- and post-therapy evaluations. These included coded, paired videotapes scored by a clinical psychologist blinded to treatment status which noted improvement in 8 of 10 children studied. Unfortunately, these gains largely waned at follow-up. Although the protocol utilized is not suggested as useful therapy, these results indicate that study of a possible "gut-flora" connection warrants further investigation as it might lead to greater pathophysiologic insight and meaningful prevention and/or treatment in a subset of children with autism.

Autism is a devastating and largely untreatable disorder currently classified as a Pervasive Developmental Disorder in the DSM-IV, it usually manifests in early infancy, with impairment typically persisting into adulthood. Incidence estimates vary from 10-20 per 10,000 children, with males four times more likely to be affected. Although some children are later found to have chromosomal aberrations or metabolic disorders which may explain their autistic features, no underlying etiology can be identified in the vast majority of cases. "Autistic regression" occurs in approximately one third of cases, with regression typically occurring before two years of age, and involving loss of language, social, and play skills.

Hypothesis

Several parents of children with regressive onset autism reported to us their observation of the following sequence: repeated broad-spectrum antimicrobial use (usually for chronic otitis media), followed by chronic diarrhea, then loss of language, play, and social skills, and subsequent onset of autistic symptoms. We developed the hypothesis that repeated antimicrobial use may have disrupted a protective effect of indigenous intestinal organisms and allowed colonization by one or more neurotoxin-producing species. If this were true, then appropriately targeted antimicrobial therapy might reduce autistic symptoms in these individuals. The most plausible candidate organisms appear to be one or more clostridial species.

Treatment Rationale

If, in fact this conjecture were correct, therapeutic options would include metronidazole, bacitracin, or vancomycin. The latter was chosen for its efficacy, minimal absorption (i.e., the antibiotic remains in the intestinal tract and is excreted in the stool), and benign taste (the unpleasant tasting metronidazole or bacitracin would have required a nasogastric tube for drug delivery). The decision to use vancomycin was not made lightly, however, since this drug is of paramount importance in treating life-threatening antibiotic-resistant bacterial infections, and significant public health concerns exist should its use become widespread in the community.

Index Case

The index case was a 4.5 year old Caucasian male with chronic diarrhea and autism whose motor, cognitive, and social development was normal until 18 months of age. Diarrhea began at approximately 17 months of age after three 10 day courses of broad spectrum antimicrobials prescribed over a six week period for "chronic otitis media." There was no blood or pus in the stool nor associated constitutional symptoms. At 19 months of age there was profound behavioral and developmental deterioration, along with emergence of severe autistic features.

Extensive genetic, neurologic, gastrointestinal, and immunologic evaluations were all unrevealing. Neither conventional (e.g., full-day special education program, speech and play therapy) nor unconventional interventions (e.g., special diets, megavitamin loading) had a significant effect on his autistic symptoms.

A 12 week therapeutic trial of oral vancomycin (125 mg QID) was begun with expanded observations by a pediatric neuropsychologist pre- and post-treatment. At baseline, the child was not on a special diet nor was he taking any vitamin supplements. Three days after initiation of the vancomycin therapy, a hyperactivity pattern emerged which lasted for four days. This was followed by two days of lethargy, and subsequently by a rapid and dramatic clinical improvement. He became affectionate and relatively calm. He promptly achieved toilet training and increased vocabulary. Follow-up behavioral observations after eight weeks of therapy noted an increase in on-task performance, compliance with parental requests, awareness of environmental surroundings, and persistence when engaging in positive activities. A significant reduction in repetitive and self-stimulatory behaviors was also noted. The child's educational therapies remained unchanged for both six months before and during the vancomycin trial. Shortly after vancomycin discontinuation, behavioral deterioration was observed. Though still improved over baseline, he eventually lost most of the initial gains.

Methods

Subjects and Study Design

To explore whether our index case's improvement represented a true therapeutic effect, institutional human investigation committee approval was obtained for an open-label trial in a narrowly defined subgroup of autistic children. Eleven children (10 males, 1 female; age range: 43-84 months) were enrolled. Inclusion criteria for the study were derived from our central hypothesis and index case characteristics. They include 1) Meets diagnostic criteria for Autistic Disorder (DSM IV 299.00); 2) Other genetic and medical diagnoses have been adequately evaluated and ruled out; 3) Definable, rapid onset after 12 months of age; 4) Antecedent antimicrobial use (<2 months of autism symptom onset); 5) Persistent loose stool history, with diarrhea onset before autism symptoms; 6) Symptoms for <4 years; 7) Child is 2-8 years of age; 8) No evidence of any significant medical problem that might complicate treatment such as renal, cardiac or pulmonary disease, severe enterocolitis (visible blood or pus in the stool), or chronic infection (e.g., tuberculosis); and 9) Clinically static for 3 months (no new neuroleptic, seizure, or other medications), with no elective changes during the study, and 10) No antimicrobial use for at least 2 months prior to entry into the study. All children had diarrhea and regressive onset of autistic features (occurring at a mean of 17.7±3.4 months) as previously defined in the literature.

The Developmental Profile II provided descriptive developmental levels to contrast with developmental age. While mean chronological age of the children was 59.4±12.7 months, the mean developmental age for the domains of communication (23.0 months±13.0), socialization (25.6 months±12.9), and self-help (34.4±12.4) are evidence of their significant developmental delay. The Childhood Autism Rating Scale (CARS) was also administered. The CARS is a 15-item behavioral rating scale developed to identify children with autism, and to distinguish them from developmentally handicapped children without the autism syndrome. Based upon CARS diagnostic categories, six children met the criteria for severe autism, two for moderate autism, and three for mild autism. The vancomycin dose was 500 mg/day given orally as a liquid (500 mg/6 ml), divided 2 ml TID for eight weeks. This was followed by four weeks of oral treatment with a probiotic mixture of *Lactobacillus acidophilus, L. bulgaricus*, and *Bifidobacterium bifidum* ($40 \times 10^9$ cfu/ml).

Psychological Evaluations

Two measures of potential improvement were examined: I) Children were videotaped for 30 minutes at baseline and once during therapy in a playroom environment. At each session, the child was directed to play with a series of puzzles, books, blocks, and dolls by the mother and then by the evaluator. At the end of the trial, a clinical child psychologist (who was provided with a brief explanation of our working hypothesis) compared coded, paired videotapes of 10 of the 11 children studied (video was not available for one child). The psychologist viewed each pair of tapes and scored them. To diminish the possibility of investigator bias, the tapes were randomly numbered and the psychologist did not have any personal contact with the children. 2) Behavior and communication analog rating scales were completed by the study physician at baseline, during therapy, and at follow-up in a manner similar to previously validated methods for other disease states. Results are presented as median scores to account for potential non-linear score increment.

Laboratory Evaluations

Extensive medical evaluations were conducted in parallel with the detailed psychological assessments. Stools were examined for occult blood, inflammatory cells, *Aeromonas hydrophila, Cryptosporidium, Clostridium difficile* toxin, routine bacterial pathogens, and ova and parasites. Blood tests included complete blood cell counts, chemistry panels, and erythrocyte sedimentation rates. Urinalyses were also obtained. Detailed quantitative aerobic and anaerobic fecal microbiologic studies were conducted at the Wadsworth Anaerobic Bacteriology Laboratory on specimens from four children. Each stool was cultured with a total of 27 different media and atmospheric conditions, modified from the procedure described in Summanen et al.

Results

Analog Rating Scales, Videotapes, Treatment Observations and Laboratory Evaluations Unblinded assessment using a analog rating scale noted improvement for the group as a whole in communication (Wilcoxon Signed Ranks Z=2.9 p=0.003) and behavior (Wilcoxon Signed Ranks Z=−2.9, p=0.003). To insure that changes attributed to intervention were not a reflection of differences at baseline, Spearman correlations were conducted. There were no significant correlations between the baseline measure and post-intervention score for either communication (rho=0.35, p=0.28) or behavior (rho=0.22, p=0.51). Blinded assessment of the coded, paired videotapes noted an improvement during therapy in eight of ten children studied, no change in one, and a possible deterioration in one.

As previously observed in the index case, a brief (1-4 days) period of hyperactivity was noted in six children within three days of initiating antibiotic treatment. One subject then experienced a day of marked lethargy. Otherwise, aside from obvious autistic features, all children had normal physical examinations at baseline and throughout the study, as well as unremarkable basic blood, stool, and urine tests as outlined in the Methods section.

Long-Term Follow-Up

Although apparent improvement was clear by several measures, unfortunately these gains did not endure. One child who had responded significantly to treatment, deteriorated towards the end of the study while still on vancomycin therapy. During telephone follow-up (conducted weekly during the probiotic therapy), most parents reported substantial behavioral deterioration within two weeks of discontinuance of vancomycin treatment. Due to difficulty in disguising the taste, probiotic treatment compliance was very poor in several children. Behavioral deterioration appeared to occur whether or not the child was compliant with the probiotic therapy regimen. Therefore, it would appear that the probiotic therapy used as an adjunct after vancomycin treatment had no discernible beneficial or adverse effect. All children were observed in follow-up, ranging from two to eight months after discontinuance of vancomycin. In all but one child, the analog ratings returned towards baseline.

Quantitative Fecal Flora

Given the extreme labor intensiveness of such studies, it will be some time before detailed microbiologic analysis of all pre- and post-therapy stool specimens is completed. Stool specimen data from four autistic children prior to vancomycin therapy were compared to those of 104 normal adult subjects from previously published studies (performed under the supervision of the same principal investigator). Anaerobic cocci, chiefly peptostreptococcal species, were present in 93% of the adults' specimens, comprising some 10% of the stool microorganisms. In stark distinction, these species were absent from the stools of each of the four autistic children tested (Table 5).

TABLE 5

Fecal Flora Data

| Organism | Autistic Patient A | Autistic Patient B | Autistic Patient C | Autistic Patient D | Adults (104 Subjects*) |
|---|---|---|---|---|---|
| Enterobacteriaceae | 6 | 7 | 7 | 7 | 9 |
| Streptococcus | 3 | 5 | 0 | 4 | 9 |
| Enterococcus | 0 | 6 | 0 | 0 | 8 |
| Bacteroides fragilis grp | 8 | 8 | 9 | 8 | 11 |
| Bacteroides, other | 8 | 0 | 9 | 8 | 11 |
| Anaerobic GNR, other | 6 | 4 | 7 | 5 | 8 |
| Peptostreptococcus spp. | 0 | 0 | 0 | 0 | 10** |
| Anaerobic cocci, other | 0*** | 0 | 0**** | 0 | 11** |
| Lactobacillus spp. | 9 | 9 | 10 | 8 | 10 |
| Bifidobacterium spp. | 7 | 9 | 9 | 8 | 10 |
| Eubacterium spp. | 8 | 0 | 9 | 8 | 11 |
| Clostridium spp. | 9 | 7 | 8 | 8 | 10 |

Units are $\log_{10}$ colony forming units (cfu) gram dry weight.
*Mean of positive specimens. Subjects were normal adults on various diets (vegetarian, traditional Japanese diet, or standard Western diet); there were no statistically significant differences in the results between these various groups.
**93% of the 104 subjects had Peptostreptococcus spp. and/or other anaerobic cocci.
***Ethanol and heat-resistant coccoid forms were present (probably clostridia.)
****Heat-resistant coccoid forms were present (probably clostridia.)

Discussion

The apparent, though short-term, improvement during treatment with this minimally absorbed antibiotic is not explainable using current conventional genetic hypotheses alone for autism. Results of this preliminary study, along with previous reports of increased intestinal permeability and a "nonspecific colitis" in children with autism, suggests a possible "gut-brain" etiologic connection may be present in a subset of these children.

Although the hypothesis that autism (in a defined subset of children) may be a sequela to the colonization of the intestinal tract by one or more neurotoxin-producing bacteria is novel, published data along several paths may lend credence to the notion that an alteration in colonic flora contributes to autism symptoms. The first line of evidence is from the infant botulism literature. This condition was first recognized as a distinct clinical entity in 1976. It differs from classical (food-borne) botulism in that the intestinal tract becomes colonized by *Clostridium botulinum* and elaboration of the neurotoxin occurs in vivo. Age is a primary risk factor for the development of infant botulism as diagnosis of the disease is rare after 1 year of age.[ii] Studies in animals have demonstrated a similar age-dependent susceptibility. However, the colonization resistance observed in mature animals is greatly diminished when they are treated with broad-spectrum antimicrobials. Similarly, antimicrobial use has been identified as a risk factor for the development of botulism related to intestinal colonization with *C. botulinum* in older children and adults.[iii]

The second line of evidence is from human and animal studies which have repeatedly demonstrated that intestinal colonization by opportunistic pathogens (e.g., *Escherichia coli, Klebsiella pneumoniae, Pseudomonas aeruginosa, Salmonella enteritidis, Shigella flexneri,* and *Vibrio cholerae*) is greatly enhanced when protective intestinal microbiota is disrupted by broad-spectrum antimicrobials. In humans, the best-documented example of opportunistic colonization of the intestinal tract following antimicrobial use is that by *Clostridium difficile*, the causative agent of pseudomembranous colitis.

Another potentially relevant condition is d-lactic acidosis, in which associated psychiatric symptoms are well-documented. D-lactic acidosis, a complication of short bowel syndrome or intestinal bypass surgery for obesity, is a condition caused by a change in bacterial flora to an acid-tolerant, aciduric (*Lactobacillus, Bifidobacterium, Eubacterium*, and *Streptococcus*) flora. Patients present with a range of behavioral changes such as hostility, slurred speech, stupor, altered mental status, dizziness, asterixis, and ataxia. Treatment is with oral antimicrobials, resulting in rapid cessation of neurological signs.

No validated instrument is currently available for quantitative measurement of improvement in autistic symptomatology and there is a major need to correct this deficit for use in future autism intervention trials. In the absence of a pre-existing standardized method, the current study utilized two independent assessment tools. Although the analog rating scales were completed by the study physician who was aware of the children's treatment status, the formal videotape ratings were performed in a blinded manner. The improvement observed after vancomycin intervention appeared to be significantly greater than could normally be attributable to the characteristic waxing and waning of autistic symptomatology.

A substantial deterioration of the behavioral improvements made while on therapy was reported by most parents within two weeks of ending the vancomycin trial. While the cause for neither the apparent improvement nor the later decline is known, it is possible the deterioration is due to the offending organism being spore-forming, and hence surviving therapy to germinate after vancomycin discontinuation, as has been documented with *Clostridium difficile* infection. An additional possibility is that the therapy was sublethal due to antimicrobial choice and/or dosage regimen permitting emergence of an antimicrobial-resistant bacteria.

Since vancomycin is not absorbed, it appears likely that the behavioral improvement was related, in some way, to the drug's effect on the intestinal tract flora (and not a "drug effect" per se on the central nervous system). Although we theorize that the transient benefit from vancomycin treatment may be due to the temporary elimination of a neurotoxin-producing pathogen, there are other possible mechanisms. For example, autoantibodies to neuron-axon filament protein, glial fibrillary acidic protein, and myelin basic protein have been reported in autism and it has been postulated that these autoantibodies may contribute to autistic symptomotology. It is, at least, theoretically possible that the production of these autoantibodies is related to the presence of an infectious pathogen as has been postulated for rheumatoid arthritis.

The significance of the possible fecal flora changes in these autistic children is unknown. It is unlikely that specimen collection or shipping contributed to the absence of *Peptostreptococcus* and other anaerobic cocci as other equally oxygen-sensitive organisms were recovered. Although all of the children had previously received broad-spectrum antimicrobials (capable of severely disrupting intestinal flora), fecal bacterial counts typically return to their pre-treatment composition within two weeks of discontinuance of the antimicrobial agent.[iv] Therefore, since none of the children, at base line, had a history of antimicrobial treatment for at least two months prior to entering our study, it is unlikely that the absence of these species reflects a transient alteration in the children's fecal flora. An uncharacterized *Peptostreptococcus* species has been documented to certain organisms, including clostridia, in vitro and in animals, and it is intriguing to speculate that the absence of such organisms in certain autistic children may permit growth of clostridial or other toxin-producing bacteria through loss of competitive inhibition.

The fecal flora of pediatric subjects has been extensively studied. Use of normal adult control fecal specimens in the present study, though not ideal, is justifiable given documented similarity to pediatric stool flora. For example, one recent review of bacterial colonization patterns states that "by 12 months (of age) the anaerobic fecal populations begin to resemble that of adults in number and composition as the facultative anaerobes decrease. By two years of age, the profile resembles that of the adult."

Example 2

Culture Conditions, Antimicrobial Susceptibility Determination

Culture Conditions

We use a selective medium for clostridia that contains (per liter) 25.0 g of brain heart infusion (BBL, USA), 20.0 g of agar (Sigma, USA), 76.0 mg of sulfamethoxazole, 4.0 mg of trimethoprim, 1.0 mg of vitamin K, 5.0 mg of hemin, and 50.0 ml of lakes sheep blood. All medium components except the two antimicrobial agents and the laked sheep blood are mixed, autoclaved at 121 deg C. for 15 mins and cooled to 50° C. in a water bath, at which point the three initially omitted ingredients are added. An additional medium is made up in identical fashion except that 30.0 to 50.0 g of agar is used, rather than 20.0, in order to make the medium stiffer and thus minimize spreading of clostridial colonies.

Stock solutions of antimicrobials are prepared separately in advance by aseptically dissolving the sulfamethoxazole in half volume hot water with a minimal amount of 2.5 M NaOH and the trimethoprim in 0.05 N lactic acid or HCl, 10% of final volume. The stock solutions are stored at −20° C. before addition to the selective medium. After the medium is poured into Petri dishes, the plates are dried and placed into an anaerobic chamber and reduced for approximately 24 hours. They are then stored in the chamber at ambient temperature (25° C.) for at least two days, but no longer than seven days, before use.

The entire stool specimen is weighed before processing. It is then placed into an anaerobic chamber and homogenized in a heavy duty blender with no diluent (if liquid) or with one or two volumes of diluent (0.05% yeast extract) added if the stool is soft or fully formed. Homogenization is carried out because we have found previously that organisms are not distributed evenly throughout the fecal mass; this avoids sampling errors. Serial ten-fold dilutions of the specimen are then made in 9 ml dilution blanks (Anaerobe Systems, USA) and 100 µl of each dilution from $10^{-1}$ through $10^{-8}$ is inoculated onto the selective medium (both agar concentrations) and onto a *Brucella* blood agar plate. The fecal suspensions ($10^{-1}$-$10^{-5}$) are also heated at 80° C. for 10 minutes (to select out clostridial spores) and 100 µl of each dilution is inoculated onto the selective media and the *Brucella* blood agar.

After 5 days of incubation of the inoculated plates at 37° C., each colony type from both heat-treated and non-treated specimens is counted from a dilution plate containing between 30 and 300 colonies of the type being isolated. Total bacterial counts, in addition to clostridial counts, are also recorded from the *Brucella* blood agar plates.

In order to correct for differing moisture content in different specimens of stool, a portion of sample (~1 g) is placed onto a pre-weighed drying dish. The dish is again weighed and then placed into a drying oven and incubated at 70° C. (with 18-20 inch Hg vacuum) for 48 hours. After this incubation, the dish with the specimen is re-weighed so that bacterial counts can be corrected for moisture content.

Identification of Isolated Bacteria

The identification of isolated colonies as clostridia, and specification of these, is done by methods outlined in the Wadsworth Anaerobic Bacteriology Manual, 5th Edition (Summanen et al., Star Publ. Co., Belmont, Calif., 1993, herein incorporated by reference) including, when indicated, cellular fatty acid analysis in a MIDI capillary column gas chromatograph, 16S rDNA sequencing, and DNA-DNA hybridization (the latter two procedures as outlined in a paper from this laboratory (Wexler H M et al., *Int. J. Syst Bacteriol* 46:252-258, 1996, herein incorporated by reference).

Antimicrobial Susceptibility Determination

Testing of susceptibility of isolated clostridia to antimicrobial agents such as vancomycin, melronidazole, bacitracin and ramoplanin is done by two different techniques—the NCCLS Wadsworth agar dilution procedure (Methods for Antimicrobial Susceptibility Testing of Anaerobic Bacteria, Approved Standard-Fourth Edition. NCCLS Publication M 11-A4, Wayne, Pa.: NCCLS, 1997, Vol. 17, No. 22, all herein incorporated by reference) and the spiral gradient endpoint procedure (Wexler H M et al., *J Clin Microbiol* 34:170-174, 1996, herein incorporated by reference).

Example 3

Testing for Toxin Polypeptides

ELISA Testing—Rationale and Methods

Since all of the known clostridial neurotoxins share significant amino acid homology, low-level cross-reactivity of antibodies has been reported. This will allow us to detect a clostridial neurotoxin that is closely related to, but not identical with, tetanus toxin.

Media containing hydrolysates of casein the production of all known clostridial neurotoxins. Therefore, the cells were grown in Brain Heart Infusion Broth (Becton Dickinson, Sparks, Md.) supplemented with 2.5% pancreatic digest of casein (Tryptone Peptone, Becton Dickinson). After five days of growth, the culture supernatants were clarified by centrifugation at 4000×g and filter-sterilized through a 0.45 µl nitrocellulose membrane filter. Antigens from known *C. tetani* strains (ATCC 10779, 19406, 453, 9441) and tetanus toxoid (Lederle, Pearl River, N.Y.) were used for initial optimization experiments and subsequently as positive controls.

Our methods are based upon previously standardized ELISA protocols for direct competitive detection of soluble antigens (Current Protocols in Molecular Microbiology). The wells of solid-phase immunoassay microtiter plates (Biotech Diagnostic, Niguel, Calif.) are inoculated with 50 µl of antigen solution, sealed with plastic wrap and incubated overnight at room temperature. The plates are washed three times with deionized water to remove unbound antigen solution. The wells are then filled with a blocking buffer (Tween 20 0.05% and bovine serum albumin 0.25%) and incubated at room temperature for 30 minutes. The plates are again washed three times prior to addition of 50 µl of serially diluted antibody solution; 1:1000 to 1:10,000 dilutions of polyclonal IgG goat tetanus exotoxin (Fitzgerald, Concord, Mass.). Plates are sealed with plastic wrap and incubated at room temperature for D two hours. After washing, rabbit anti-goat IgG alkaline phosphatase conjugated antibodies (Fitzgerald) are added and the plates incubated at room temperature overnight. A microtiter plate reader was used to measure the fluorescence.

ELISA Results

All four ATCC strains of *C. tetani* consistently produced positive results. This is interesting to note because *C. tetani* strain ATCC 19406 does not consistently yield positive PCR results. One possible explanation may be that ATCC 19406 produces a toxin immunologically similar (or identical) to other *C. tetani* strains but its genetic code for toxin production is slightly different During initial testing, we noticed that all *C. perfringens* strains (ATCC type strain, strains from children with autism, and strains from normal children) yielded positive results. This might be due to cross-reactivity of the antibodies against tetanolysin (a hemolysin produced by *C. tetani* strains) with perfringolysin—a very closely related hemolysin. We performed Western blot testing so that the size of the immunoreactive proteins could be visualized and compared to positive controls.

Western Blot Testing

The cells were grown in Brain-Heart-Infusion Broth (Becton Dickinson, Sparks, Md.) supplemented with 2.5% pancreatic digest of casein (Tryptone Peptone, Becton Dickinson). After four days of incubation at 37° C. and an additional two days at 4° C. (to enhance sporulation, lysis and release of toxin), the culture supernatants are clarified by centrifugation at 4000×g and filter-sterilized through a 0.45 µm nitrocellulose membrane filter. *Clostridium tetani* strains (ATCC 10779, 19406, 453, 9441) and tetanus toxoid (Lederle, Pearl River, N.Y.) were used for initial optimization experiments.

Our methods are based upon previously standardized protocols for immunoblotting and immunodetection (Western blotting) of soluble antigens (Current Protocols in Molecular Microbiology, vol. 2, 1997, pp. 10.8.1-21). Briefly, the filtered culture supernatant is solubilized with a detergent (SDS) and a reducing agent is included to reduce sulfhydryl bonds. The solubilized proteins are separated by SDS-polyacrylamide gel electrophoresis (SDS-PAGE). The gel is then electroblotted resulting in transfer of the protein bands to a nitrocellulose membrane. The membrane is placed in a tray with blocking buffer, 2% skim milk in phosphate-buffered saline (PBS), and kept at room temperature for 1 hour. Primary antibody, polyclonal IgG goat tetanus antitoxin (Fitzgerald, Concord, Mass.), diluted 1:1,000 in blocking buffer is then added. Following a 1-hour incubation, the membrane is washed four times with PBS. The detection of antibody binding occur with rabbit anti-goat-IgG conjugated to alkaline phosphatase. When substrate is added, a calorimetric reaction occurs, thus indicating that the initial (anti-tetanus serum) antibody was bound by a protein on the membrane. (Sigma, St. Louis, Mo.) Anti-Ig conjugate, 1:1,000 dilution in blocking buffer, is added and incubated at room temperature for 1 hour. After four fifteen-minute washes, the membrane is incubated with color development buffer (100 mg/ml 4-nitro blue tetrazolium chloride (final: 0.33 mg/ml) (NBT) and 50/mg/ml 5-bromo-4-chloro-3-indolyl-phosphate (final: 0.165 mg/ml) (BCIP) added to substrate buffer: 0.05M $Na_2CO_3$, 0.5 mM $MgCl_2$ pH 10.2). The reaction is stopped by washing the membrane in distilled water for 10 minutes.

Western Blot Results

We initially tested multiple *C. perfringens* strains; the ATCC type strain, a strain isolated from the stool of a child with autism, and a strain isolated from the stool of a normal child. All strains of *C. perfringens* produced an immunoreactive protein of the same molecular weight, which explains the positive results observed during ELISA testing. We theorize that this protein may be perfringolysin (which would be expected to cross react with anti-tetanolysin antibodies). There were, however, striking differences between these three *C. perfringens* strains. The strain from the autistic child produced additional immunoreactive proteins. Furthermore, these immunoreactive proteins appeared to be of the same molecular weight as the tetanus neurotoxin proteins (light and heavy chain, about 100 kD) produced by our *C. tetani* control strain. Repeat testing confirmed our initial results. Additional studies were performed on several clostridial species isolated from a second child with autism. One of the strains from this child, *C. beijerinckii*, produced a strongly immunoreactive protein of ~50 kDa, which is the approximate weight of the light-chain of tetanus toxin and other known clostridial neurotoxins. Western blot testing of the ATCC *C. beijerinckii* type strain will be performed. However, ELISA testing of the type strain was negative, suggesting that typical *C. beijerinckii* strains do not produce a protein that is immunoreactive with anti-tetanus antibodies.

Our colleague, has tested the filtrate of an ATCC strain of *C. tetani* in the hind leg of mice and has produced paralysis of that limb and subsequently death. We will test blinded cultures from autistic and control children for this in vivo test.

The invention claimed is:

1. A method of treating autism associated with colonization of pathogenic bacteria in the gastrointestinal tract of a patient with early onset autism, said method comprising administering to the patient suffering from autism a treatment course of an effective amount of metronidazole, bacitracin, or vancomycin thereby treating autism associated with colonization of pathogenic bacteria in the gastrointestinal tract of a patient, and wherein the treatment alleviates autistic symptoms.

2. A method of treating autism associated with colonization of pathogenic bacteria in the gastrointestinal tract of a patient with early onset autism, said method comprising administering to the patient suffering from autism a treatment course of an effective amount of metronidazole, bacitracin, or vancomycin thereby treating autism associated with colonization of pathogenic bacteria in the gastrointestinal tract of a patient, wherein the treatment alleviates autistic symptoms, and wherein the patient was administered an antimicrobial agent prior to onset of autism, wherein the antimicrobial agent is not metronidazole, bacitracin, or vancomycin.

3. The method of claim 2, wherein the patient was administered an antimicrobial agent two months prior to onset of autism.

4. The method of claim 2, wherein the patient was administered an antimicrobial agent less than two months prior to onset of autism.

5. The method of claim 2, wherein pathogenic bacterial colonization is by neurotoxin-producing species of bacteria.

* * * * *